United States Patent [19]

Flockerzi

[11] Patent Number: 5,064,839
[45] Date of Patent: Nov. 12, 1991

[54] 1,4-DIHYDROPYRIDINES WITH A 2-AMINO GROUP OR WITH AN ETHER GROUP IN A SIDE CHAIN

[75] Inventor: Dieter Flockerzi, Allensbach, Fed. Rep. of Germany

[73] Assignee: Byk Gulden Lomberg Chemische Fabrik GmbH, Constance, Fed. Rep. of Germany

[21] Appl. No.: 272,775
[22] PCT Filed: Apr. 17, 1987
[86] PCT No.: PCT/EP87/00210
    § 371 Date: Oct. 21, 1988
    § 102(e) Date: Oct. 21, 1988
[87] PCT Pub. No.: WO87/06579
    PCT Pub. Date: Nov. 5, 1987

[30] Foreign Application Priority Data

Apr. 22, 1986 [CH] Switzerland ............ 01623/86
Apr. 22, 1986 [CH] Switzerland ............ 01633/86

[51] Int. Cl.$^5$ ............ C07D 401/04; C07D 401/14; A61K 31/44; A61K 31/445
[52] U.S. Cl. ............ 514/318; 546/257; 546/194; 546/193; 546/271
[58] Field of Search ............ 546/321, 257, 194, 193; 514/318

[56] References Cited

U.S. PATENT DOCUMENTS

| 3,849,396 | 11/1974 | Birkenmeyer | 260/210 R |
| 3,849,576 | 11/1974 | Kalopissis | 514/665 |
| 3,852,279 | 12/1974 | Krapcho | 546/119 |
| 4,387,099 | 6/1983 | Smith | 546/294 |
| 4,387,219 | 6/1983 | Yamamoto | 536/13.6 |
| 4,395,414 | 7/1983 | Eistetter | 514/312 |
| 4,686,230 | 8/1987 | Rainer | 514/338 |
| 4,758,579 | 7/1988 | Kohl | 514/338 |
| 4,886,819 | 12/1989 | Ashimori | 514/356 |

Primary Examiner—Alan L. Rotman
Attorney, Agent, or Firm—Berman & Aisenberg

[57] ABSTRACT

New amines and ethers of the formula I

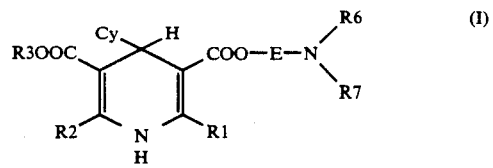

wherein the substituents and symbols have the meanings given in the description, are new compounds with surprising pharmacological properties.

12 Claims, No Drawings

1,4-DIHYDROPYRIDINES WITH A 2-AMINO GROUP OR WITH AN ETHER GROUP IN A SIDE CHAIN

FIELD OF APPLICATION OF THE INVENTION

The invention relates to new amines and ethers, processes for their preparation, their use and medicaments containing them. The compounds according to the invention are used in the pharmaceutical industry for the preparation of medicaments.

KNOWN TECHNICAL BACKGROUND

Certain 1,4-dihydropyridine derivatives substituted in various ways have pharmacologically beneficial properties. Surprisingly, it has now been found that the new compounds described in more detail below have particularly interesting pharmacological properties by which they differ advantageously form the compounds of the prior art.

DESCRIPTION OF THE INVENTION

The invention relates to new amines and ethers of formula I

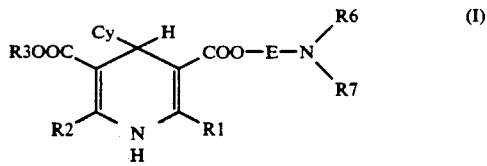

wherein Cy represents a cyclic radical of the formula

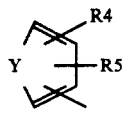

in which Y denotes oxygen (O), sulfur (S), vinylene (—CH=CH—), azomethine (—CH=N—) or a group of the formula

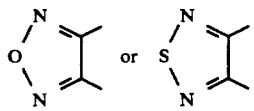

R1 denotes hydrogen 1–6C-alkyl or 3–7C-alkoxyalkyl,

R4 and R5 are identical or different and denote hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, R6 and R7, together and including the nitrogen atom to which the two are bonded, represent a radical of the formula

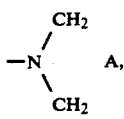

wherein
A denotes —CH$_2$—C(R8)R9—CH$_2$—,
R8 denotes aryl and
R9 denotes aryl,
aryl representing a ring of the formula

wherein R10 and R11 are identical or different and denote hydrogen (H), 1–4C-alkyl, 1–4C-alkoxy, halogen, hydroxyl or trifluoromethyl, and wherein either
E denotes 2–5C-alkylene,
R2 denotes amino (NH$_2$) and
R3 denotes 1–6C-alkyl or 3–7C-alkoxyalkyl, or
E denotes A1—O—A2,
R2 denotes hydrogen, 1–6C-alkyl or 3–7C-alkoxyalkyl and
R3 denotes hydrogen, 1–6C-alkyl or 3–7C-alkoxyalkyl and
in which
A1 denotes 2–4C-alkylene and
A2 denotes 2–4C-alkylene or 2C-alkyleneoxy-2C-alkylene,
and the salts of these compounds.

1–6C-Alkyl is straight-chain or branched and denotes, for example, a hexyl, neopentyl, isopentyl, butyl, i-butyl, sec.-butyl, t-butyl, propyl, isopropyl or, in particular, ethyl or methyl radical.

3–7C-Alkoxyalkyl represents, for example, an ethoxyethyl, propoxyethyl, isopropoxyethyl, butoxyethyl, methoxypropyl, 2-methoxy-1-methylethyl, 2-ethoxy-1-methylethyl or, in particular, methoxyethyl radical.

Halogen in the context of the invention denotes bromine, fluorine or, in particular, chlorine.

1–4C-Alkyl is straight-chain or branched and denotes, for example, a butyl, i-butyl, sec.-butyl, t-butyl, propyl, isopropyl, ethyl or, in particular, methyl radical.

In addition to the oxygen atom, 1–4C-alkoxy contains one of the abovementioned 1–4C-alkyl radicals. The methoxy and the ethoxy radical are preferred.

1–4C-Alkoxy which is completely or partly substituted by fluorine is, for example, 1,1,2,2-tetrafluoroethoxy, trifluoromethoxy, 2,2,2-trifluoroethoxy or, in particular, difluoromethoxy.

In addition to the carbonyl group, 1–4C-alkoxycarbonyl contains one of the abovementioned 1–4C-alkoxy radicals. The methoxycarbonyl and the ethoxycarbonyl radical are preferred.

In addition to the carbonyl group, 2–5C-acyl contains one of the abovementioned 1–4C-alkyl radicals. The acetyl radical is preferred.

In addition to the nitrogen atom, mono- or di-1–4C-alkylamino contains one or two of the abovementioned 1–4C-alkyl radicals. Di-1–4C-alkylamino is preferred, and here in particular dimethyl-, diethyl- or diisopropylamino.

Aryl represents phenyl which is substituted by R10 and R11. Examples which may be mentioned of preferred aryl radicals are the radicals: phenyl, 4-methoxyphenyl, 4-chlorophenyl, 4-methylphenyl, 4-fluorophenyl, 3-fluorophenyl, 3-chlorophenyl, 2-chlorophenyl, 3-methoxyphenyl, 2-methoxyphenyl, 2-methylphenyl, 3-chloro-4-methylphenyl, 3,4-dichlorophenyl, 3,6- dichlorophenyl, 3,4-dimethylphenyl, 2-trifluoromethylphenyl and 3-trifluoromethylphenyl.

2-5C-Alkylene is straight-chain or branched and represents, for example, ethylene (—CH$_2$—CH$_2$—), trimethylene (—CH$_2$—CH$_2$—CH$_2$—), tetramethylene (—CH$_2$—CH$_2$—CH$_2$—CH$_2$—), pentamethylene (—CH$_2$—CH$_2$—CH$_2$—CH$_2$—CH$_2$—), 1,2-dimethylethylene, 1,1-dimethylethylene, 2,2-dimethylethylene, isopropylidene, 1-methylethylene or 2-ethylpropylene, ethylene and trimethylene being preferred.

2-4C-Alkylene represents ethylene (—CH$_2$—CH$_2$—), trimethylene (—CH$_2$—CH$_2$—CH$_2$—) or tetramethylene (—CH$_2$—CH$_2$—CH$_2$—CH$_2$—), ethylene being preferred.

2C-Alkyleneoxy-2C-alkylene represents ethylene which is substituted by ethyleneoxy (—CH$_2$CH$_2$—O—CH$_2$—CH$_2$—).

Possible salts are all the salts with acids. The pharmacologically-acceptable salts of the inorganic and organic acids usually employed in the pharmaceutical industry may be mentioned in particular. Pharmacologically-acceptable salts, which may initially be obtained, for example, as process products in the preparation of the compounds according to the invention on an industrial scale, are converted into pharmacologically-acceptable salts by processes which are known to the expert. Such suitable salts are, for example, water-soluble and water-insoluble acid-addition salts, such as the hydrochloride, hydrobromide, hydriodide, phosphate, nitrate, sulfate, acetate, citrate, gluconate, benzoate, hibenzate, fendizoate, butyrate, sulfosalicylate, maleate, laurate, malate, fumarate, succinate, oxalate, tartrate, amsonate, metembonate, stearate, tosylate, 2-hydroxy-3-naphthoate, 3-hydroxy-2-naphthoate or mesylate, as well as salts with bumetanide, furosemide, azosemide, galosemide, besunide, piretanide, etacrynic acid, tienilic acid or 4-chlorosulfamoyl-benzoic acid.

One embodiment of the invention (embodiment a) comprises compounds of formula Ia

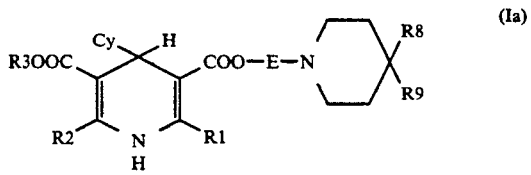

(Ia)

wherein Cy represents a cyclic radical of the formula

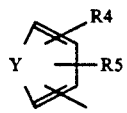

in which Y denotes oxygen (O), sulfur (S), vinylene (—CH=CH—), azomethine (—CH=N—) or a group of the formula

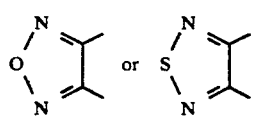

E denotes 2-5C-alkylene,
R1 denotes hydrogen 1-6C-alkyl or 3-7C-alkoxyalkyl,
R2 denotes amino (NH$_2$),
R3 denotes 1-6C-alkyl or 3-7C-alkoxylalkyl,
R4 and R5 are identical or different and denote hydrogen, hydroxyl, halogen, nitro, cyano, trifluoromethyl, 1-4C-alkyl, 1-4C-alkoxy, 1-4C-alkoxy which is completely or partly substituted by fluorine, 1-4C-alkoxycarbonyl, 2-5C-acyl, amino or mono- or di-1-4C-alkylamino,
R8 denotes aryl and
R9 denotes aryl,
aryl representing a ring of the formula

wherein R10 and R11 are identical or different and denote hydrogen (H), 1-4C-alkyl, 1-4C-alkoxy, halogen, hydroxyl or trifluoromethyl, and the salts of these compounds.

Compounds of embodiment a which are to be singled out are those of the formula Ia wherein
Cy denotes phenyl, 2-nitrophenyl, 3-nitrophenyl, 2-cyanophenyl, 3-cyanophenyl, 2-(1,1,2,2-tetrafluoroethoxy)-phenyl, 3-(1,1,2,2-tetrafluoroethoxy)-phenyl, 2-difluoromethoxyphenyl, 3-difluoromethoxyphenyl, 2-chlorophenyl, 3-chlorophenyl, 2,3-dichlorophenyl, 2-fluorophenyl, 3-fluorophenyl, 2-trifluoromethylphenyl, 3-trifluoromethylphenyl or benzoxadiazolyl,
E denotes ethylene (—CH$_2$—CH$_2$—), trimethylene (—CH$_2$—CH$_2$—CH$_2$—), or pentamethylene (—CH$_2$—CH$_2$—CH$_2$—CH$_2$—CH$_2$—),
R1 denotes methyl,
R2 denotes amino (NH$_2$),
R3 denotes methyl, ethyl or methoxyethyl,
R8 denotes aryl and
R9 denotes aryl,
aryl representing a ring of the formula

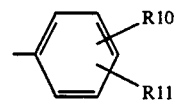

wherein R10 and R11 are identical or different and denote hydrogen (H), methyl, methoxy, chlorine, fluorine, hydroxyl or trifluoromethyl, and the salts of the compounds. Preferred compounds of embodiment a are those of the formula Ia wherein
Cy denotes phenyl, 3-nitrophenyl, 2-cyanophenyl, 2,3-dichlorophenyl, 2-trifluoromethylphenyl or benzoxadiazolyl,
E denotes ethylene (—CH$_2$—CH$_2$—), trimethylene (—CH$_2$—CH$_2$—CH$_2$—) or pentamethylene (—CH$_2$—CH$_2$—CH$_2$—CH$_2$—CH$_2$—),
R1 denotes methyl,
R2 denotes amino (NH$_2$),
R3 denotes methyl or ethyl,
R8 denotes phenyl and
R9 denotes phenyl
and their salts.

Particularly preferred compounds of embodiment a are those of the formula Ia wherein
Cy denotes 3-nitrophenyl, E denotes ethylene (—CH₂—CH₂—) or trimethylene (—CH₂—CH₂—CH₂—), R1 denotes methyl,
R2 denotes amino (NH₂),
R3 denotes methyl or ethyl,
R8 denotes phenyl and
R9 denotes phenyl,
and their salts.

Examples which may be mentioned of compounds of embodiment a are:

3-ethyl 5-[2-(4,4-diphenylpiperid-1-yl)-ethyl] 2-amino-1,4-dihydro-6-methyl-4-(3-nitrophenyl)-pyridine-3,5-dicarboxylate, 3-(2-methoxyethyl) 5-[3-(4,4-diphenylpiperid-1-yl)-propyl] 2-amino-1,4-dihydro-6-methyl-4-(3-nitrophenyl)-pyridine-3,5-dicarboxylate, 3-methyl 5-[4-(4,4-diphenylpiperidyl-1)-butyl] 2-amino-1,4-dihydro-6-methyl-4-(3-nitrophenyl)-pyridine-3,5-dicarboxylate, 3-methyl 5-[2-(4,4-diphenylpiperid-1-yl)-ethyl] 2-amino-1,4-dihydro-6-methyl-4-(2-nitrophenyl)-pyridine-3,5-dicarboxylate, 3-methyl 5-[2-(4,4-diphenylpiperid-1-yl)-ethyl] 2-amino-1,4-dihydro-6-ethyl-4-(3-nitrophenyl)-pyridine-3,5-dicarboxylate, 3-(prop-2-yl) 5-[2-(4,4-diphenylpiperid-1-yl)-ethyl] 2-amino-1,4-dihydro-6-methyl-4-(3-nitrophenyl)-pyridine-3,5-dicarboxylate, 3-hexyl 5-[2-(4,4-diphenylpiperid-1-yl)-ethyl] 2-amino-1,4-dihydro-6-methyl-4-(3-nitrophenyl)-pyridine-3,5-dicarboxylate, 3-(2-n-butoxyethyl) 5-[2-(4,4-diphenylpiperid-1-yl)-ethyl] 2-amino-1,4-dihydro-6-methyl-4-(3-nitrophenyl)-pyridine-3,5-dicarboxylate, 3-methyl 5-{2-[4,4-di(4-methoxyphenyl)-piperid-1-yl]-ethyl} 2-amino-1,4-dihydro-6-methyl-4-(3-nitrophenyl)-pyridine-3,5-dicarboxylate, 3-ethyl 5-[2-(4,4-diphenylpiperid-1-yl)-ethyl] 2-amino-1,4-dihydro-6-methyl-4-(2-trifluoromethylphenyl)-pyridine-3,5-dicarboxylate, 3-methyl 5-[2-(4,4-diphenylpiperid-1-yl)-ethyl] 2-amino-1,4-dihydro-6-methyl-4-[3-(1,1,2,2-tetrafluoroethoxy)-phenyl]-pyridine-3,5-dicarboxylate, 3-ethyl 5-[2-(4,4-diphenylpiperid-1-yl)-ethyl] 2-amino-1,4-dihydro-6-methyl-4-(2-difluoromethylphenyl)-pyridine-3,5-dicarboxylate, 3-ethyl 5-[4-(4,4-diphenylpiperid-1-yl)-ethyl] 2-amino-1,4-dihydro-6-methyl-4-(2-difluoromethylphenyl)-pyridine-3,5-dicarboxylate, 3-methyl 5-[2-(4,4-dihydroxyphenylpiperid-1-yl)-ethyl] 2-amino-1,4-dihydro-6-methyl-4-(3-nitrophenyl)-pyridine-3,5-dicarboxylate, 3-methyl 5-[2-(4,4-diphenylpiperid-1-yl)-ethyl] 2-amino-4-(2,3-dichlorophenyl)-1,4-dihydro-6-methylpyridine-3,5-dicarboxylate, 3-methyl 5-[2-(4,4-diphenylpiperid-1-yl)-ethyl] 2-amino-4-(2,1,3-benzoxadiazol-4-yl)-1,4-dihydro-6-methylpyridine-3,5-dicarboxylate, 3-methyl 5-[2-(4,4-diphenylpiperid-1-yl)-ethyl] 2-amino-4-(3-cyanophenyl)-1,4-dihydro-6-methylpyridine-3,5-dicarboxylate, 3-methyl 5-[2-(4,4-diphenylpiperid-1-yl)-ethyl] 2-amino-1,4-dihydro-6-methyl-4-(2-methoxyphenyl)-pyridine-3,5-dicarboxylate, 3-methyl 5-[2-(4,4-diphenylpiperidyl-1)-ethyl] 2-amino-1,4-dihydro-6-methyl-4-(2-pyridyl)-pyridine-3,5-dicarboxylate, 3-methyl 5-[2-(4,4-diphenylpiperid-1-yl)-ethyl] 2-amino-1,4-dihydro-6-methyl-4-(5-methyl-2-thienyl)-pyridine-3,5-dicarboxylate, 3-methyl 5-{2-[4-(4-chlorophenyl)-4-phenylpiperid-1-yl]-ethyl} 2-amino-1,4-dihydro-6-methyl-4-(3-nitrophenyl)-pyridine-3,5-dicarboxylate, 3-methyl 5-[3-(4,4-diphenylpiperid-1-yl)-propyl] 2-amino-1,4-dihydro-6-methyl-4-(2-nitrophenyl)-pyridine-3,5-dicarboxylate, 3-methyl 5-[3-(4,4-diphenylpiperid-1-yl)-propyl] 2-amino-1,4-dihydro-6-ethyl-4-(3-nitrophenyl)-pyridine-3,5-dicarboxylate, 3-(propyl-2) 5-[3-(4,4-diphenylpiperid-1-yl)-propyl] 2-amino-1,4-dihydro-6-methyl-4-(3-nitrophenyl)-pyridine-3,5-dicarboxylate, 3-hexyl 5-[3-(4,4-diphenylpiperid-1-yl)-propyl] 2-amino-1,4-dihydro-6-methyl-4-(3-nitrophenyl)-pyridine-3,5-dicarboxylate, 3-(2-n-butoxyethyl) 5-[3-(4,4-diphenylpiperid-1-yl)-propyl] 2-amino-1,4-dihydro-6-methyl-4-(3-nitrophenyl)-pyridine-3,5-dicarboxylate, 3-methyl 5-{3-[4,4-di(4-methoxyphenyl)-piperid-1-yl]-propyl} 2-amino-1,4-dihydro-6-methyl-4-(3-nitrophenyl)-pyridine-3,5-dicarboxylate, 3-ethyl 5-[3-(4,4-diphenylpiperid-1-yl)-propyl] 2-amino-1,4-dihydro-6-methyl-4-(2-trifluoromethylphenyl)-pyridine-3,5-dicarboxylate, 3-methyl 5-[3-(4,4-diphenylpiperid-1-yl)-propyl] 2-amino-1,4-dihydro-6-methyl-4-[3-(1,1,2,2-tetrafluoroethoxy)-phenyl]-pyridine-3,5-dicarboxylate, 3-ethyl 5-[3-(4,4-diphenylpiperid-1-yl)-propyl] 2-amino-1,4-dihydro-6-methyl-4-(2-difluoromethylphenyl)-pyridine-3,5-dicarboxylate, 3-methyl 5-[3-(4,4-dihydroxyphenylpiperid-1-yl)-propyl] 2-amino-1,4-dihydro-6-methyl-4-(3-nitrophenyl)-pyridine-3,5-dicarboxylate, 3-methyl 5-[3-(4,4-diphenylpiperid-1-yl)-propyl] 2-amino-4-(2,3-dichlorophenyl)-1,4-dihydro-6-methyl-pyridine-3,5-dicarboxylate, 3-methyl 5-[3-(4,4-diphenylpiperid-1-yl)-propyl] 2-amino-4-(2,1,3-benzoxadiazol-4-yl)-1,4-dihydro-6-methylpyridine-3,5-dicarboxylate, 3-methyl 5-[3-(4,4-diphenylpiperid-1-yl)-propyl] 2-amino-4-(3-cyanophenyl)-1,4-dihydro-6-methylpyridine-3,5-dicarboxylate, 3-methyl 5-[3-(4,4-diphenylpiperid-1-yl)-propyl] 2-amino-1,4-dihydro-6-methyl-4-(2-methoxyphenyl)-pyridine-3,5-dicarboxylate, 3-methyl 5-[3-(4,4-diphenylpiperid-1-yl)-propyl] 2-amino-1,4-dihydro-6-methyl-4-(2-pyridyl)-pyridine-3,5-dicarboxylate, 3-methyl 5-[3-(4,4-diphenylpiperid-1-yl)-propyl] 2-amino-1,4-dihydro-6-methyl-4-(5-methyl-2-thienyl)-pyridine-3,5-dicarboxylate, and 3-methyl 5-{3-[4-(4-chlorophenyl)-4-phenylpiperid-1-yl]-propyl} 2-amino-1,4-dihydro-6-methyl-4-(3-nitrophenyl)-pyridine-3,5-dicarboxylate and their salts.

Another embodiment (embodiment b) of the invention comprises compounds of formula Ib

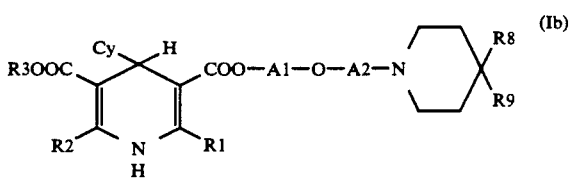

wherein Cy represents a cyclic radical of the formula

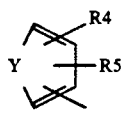

in which Y denotes oxygen (O), sulfur (S), vinylene (—CH=CH—), azomethine (—CH=N—) or a group of the formula

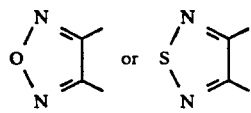

A1 denotes 2–4C-alkylene,
A2 denotes 2–4C-alkylene or 2C-alkyleneoxy-2C-alkylene,
R1 and R2 are identical or different and denote hydrogen, 1–6C-alkyl or 3–7C-alkoxyalkyl,
R3 denotes hydrogen, 1–6C-alkyl or 3–7C-alkoxyalkyl,
R4 and R5 are identical or different and denote hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino,
R8 denotes aryl and
R9 denotes aryl, wherein
aryl represents a ring of the formula

wherein R10 and R11 are identical or different and denote hydrogen (H), 1–4C-alkyl, 1–4C-alkoxy, halogen, hydroxyl or trifluoromethyl.
and the salts of these compounds.

Compounds of embodiment b which are to be singled out are those of the formula Ib wherein
Cy denotes phenyl, 2-nitrophenyl, 3-nitrophenyl, 2-cyanophenyl, 3-cyanophenyl, 2-(1,1,2,2-tetrafluoroethoxy)-phenyl, 3-(1,1,2,2-tetrafluoroethoxy)-phenyl, 2-difluoromethoxyphenyl, 3-difluoromethoxyphenyl, 2-chlorophenyl, 3-chlorophenyl, 2,3-dichlorophenyl, 2-fluorophenyl, 3-fluorophenyl, 2-trifluoromethylphenyl, 3-trifluoromethylphenyl or benzoxadiazolyl,
A1 denotes ethylene (—CH2CH2—),
A2 denotes ethylene (—CH2—CH2—) or ethyleneoxyethylene (—CH2—CH2—O—CH2—CH2—),
R1 denotes methyl,
R2 denotes methyl,
R3 denotes methyl, ethyl or methoxyethyl,
R8 denotes aryl and
R9 denotes aryl, wherein
aryl represents a ring of the formula

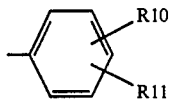

wherein R10 and R11 are identical or different and denote hydrogen (H), methyl, methoxy, chloro, fluoro, hydroxyl or trifluoromethyl, and the salts of the compounds.

Preferred compounds of embodiment b are those of the formula Ib wherein
Cy denotes 3-nitrophenyl, 2-chlorophenyl, 2,3-dichlorophenyl, 2-trifluoromethylphenyl or benzoxadiazolyl,
A1 denotes ethylene (—CH2—CH2—),
A2 denotes ethylene (—CH2—CH2—) or ethyleneoxyethylene (—CH2—CH2—O—CH2—CH2—),
R1 denotes methyl,
R2 denotes methyl,
R3 denotes methyl or ethyl,
R8 denotes phenyl and
R9 denotes phenyl
and their salts.

Particularly preferred compounds of embodiment b are those of the formula Ib wherein
Cy denotes 3-nitrophenyl,
A1 denotes ethylene (—CH2CH2—),
A2 denotes ethylene (—CH2CH2—),
R1 denotes methyl,
R2 denotes methyl,
R3 denotes methyl,
R8 denotes phenyl and
R9 denotes phenyl,
and their salts.

Examples which may be mentioned of compounds of embodiment b are:
3-ethyl 5-{2-[2-(4,4-diphenylpiperid-1-yl)-ethoxy]-ethyl} 1,4-dihydro-2,6-dimethyl-4-(3-nitrophenyl)-pyridine-3,5-dicarboxylate,
3-(2-methoxyethyl) 5-{-3-[3-(4,4-diphenylpiperid-1-yl)-propoxy]-propyl} 1,4-dihydro-2,6-dimethyl-4-(3-nitrophenyl)-pyridine-3,5-dicarboxylate,
3-methyl 5-{2-[2-(4,4-diphenylpiperid-1-yl)-ethoxy]-ethyl} 1,4-dihydro-2,6-dimethyl-4-(2-nitrophenyl)-pyridine-3,5-dicarboxylate,
3-methyl 5-{2-[2(4,4-diphenylpiperid-1-yl)-ethoxy]-ethyl} 1,4-dihydro-2,6-diethyl-4-(3-nitrophenyl)-pyridine-3,5-dicarboxylate,
3-prop-2-yl) 5-{2-[2-(4,4-diphenylpiperid-1-yl)-ethoxy]-ethyl} 1,4-dihydro-2,6-dimethyl-4-(3-nitrophenyl)-pyridine-3,5-dicarboxylate,
3-hexyl 5-{2-[2(4,4-diphenylpiperid-1-yl)-ethoxy]-ethyl} 1,4-dihydro-2,6-dimethyl-4-(3-nitrophenyl)-pyridine-3,5-dicarboxylate,
3-(2-n-butoxyethyl) 5-{2-[2-(4,4-diphenylpiperid-1-yl)-ethoxy]-ethyl} 1,4-dihydro-2,6-dimethyl-4-(3-nitrophenyl)-pyridine-3,5-dicarboxylate,
3-ethyl 5-{2-[2-(4,4-diphenylpiperid-1-yl)-ethoxy]-ethyl} 1,4-dihydro-2,6-dimethyl-4-(2-trifluoromethylphenyl)-pyridine-3,5-carboxylate,
3-methyl 5-{2-[2-(4,4-diphenylpiperid-1-yl)-ethoxy]-ethyl} 1,4-dihydro-2,6-dimethyl-4-[3-(1,1,2,2-tetrafluoroethoxy)-phenyl]-pyridine-3,5-dicarboxylate,
3-ethyl 5-{2-[2-(4,4-diphenylpiperid-1-yl)-ethoxy]-ethyl} 1,4-dihydro-2,6-dimethyl-4-(2-difluoromethoxyphenyl)-pyridine-3,5-dicarboxylate, 3-methyl 5-{2-[2-(4,4-dihydroxyphenylpiperid-1-yl)-ethoxy]-ethyl} 1,4-dihydro-2,6-dimethyl-4-(3-nitrophenyl)-pyridine-3,5-dicarboxylate, 3-methyl 5-{2-[2-(4,4-diphenylpiperid-1-yl)-ethoxy]-ethyl} 4-(2,3-dichlorophenyl)-1,4-dihydro-2,6-dimethylpyridine-3,5-dicarboxylate, 3-methyl 5-{2-[2-(4,4-diphenylpiperid-1-yl)-ethoxy]-ethyl} 4-(2,1,3-benzoxadiazol-4-yl)-1,4-dihydro-2,6-dimethylpyridine-3,5-dicarboxylate, 3-methyl 5-{2-[2-(4,4-diphenylpiperid-1-yl)-ethoxy]-ethyl} 4-(3-cyanophenyl)-1,4-dihydro-2,6-dimethyl-pyridine-3,5-dicarboxylate, 3-methyl 5-{2-[2-(4,4-diphenylpiperid-1-yl)-ethoxy]-ethyl} 1,4-dihydro-2,6-dimethyl-4-(2-methoxyphenyl)-pyridine-3,5-dicarboxylate, 3-methyl 5-{2-[2-(4,4-diphenylpiperid-1-yl)-ethoxy]-ethyl} 1,4-dihydro-2,6-dimethyl-4-(2-pyridyl)-pyridine-3,5-dicarboxylate, 3-methyl 5-{2-[2-(4,4-diphenylpiperid-1-yl)ethoxy]-ethyl} 1,4-dihydro-2,6-dimethyl-4-(5-methyl-2-thienyl)-pyridine-3,5-dicarboxylate, 3-methyl 5-{3-[3-(4,4-diphenylpiperid-1-yl)-propxyl]-propyl} 1,4-dihydro-2,6-dimethyl-4-(2-nitrophenyl)-pyridine-3,5-dicarboxylate, 3-methyl 5-{3-[3-(4,4-diphenylpiperid-1-yl)-propoxy]-propyl} 1,4-dihydro-2,6-diethyl-4-(3-nitrophenyl)-pyridine-3,5-dicarboxylate, 3-(prop-2-yl) 5-{3-[3-(4,4-diphenylpiperid-1-yl)-propoxy]-propyl} 1,4-dihydro-2,6-dimethyl-4-(3-nitrophenyl)-pyridine-3,5-dicarboxylate, 3-hexyl 5-{3-[3-(4,4-diphenylpiperid-1-yl)-propoxy]-propyl} 1,4-dihydro-2,6-dimethyl-4-(3-nitrophenyl)-pyridine-3,5-dicarboxylate, 3-(2-n-butoxyethyl) 5-{3-[3-(4,4-diphenylpiperid-1-yl)-propoxy]-propyl} 1,4-dihydro-2,6-dimethyl-4-(3-nitrophenyl)-pyridine-3,5-dicarboxylate, 3-ethyl 5-{3-[3-(4,4-diphenylpiperid-1-yl)-propoxy]-propyl} 1,4-dihydro-2,6-dimethyl-4-(2-trifluoromethyl-phenyl)-pyridine-3,5-dicarboxylate, 3-methyl 5-{3-[3-(4,4-diphenylpiperid-1-yl)-propoxy]-propyl} 1,4-dihydro-2,6-dimethyl-4-[3-(1,1,2,2-tetrafluoroethoxy)-phenyl]-pyridine-3,5-dicarboxylate, 3-ethyl 5-{3-[3-(4,4-diphenylpiperid-1-yl)-propoxy]-propyl} 1,4-dihydro-2,6-dimethyl-4-(2-difluoromethoxyphenyl)-pyridine-3,5-dicarboxylate, 3-methyl 5-{3-[3-(4,4-dihydroxyphenylpiperid-1-yl)-propoxy]-propyl} 1,4-dihydro-2,6-dimethyl-4-(3-nitrophenyl)-pyridine-3,5-dicarboxylate, 3-methyl 5-{3-[3-(4,4-diphenylpiperid-1-yl)-propoxy]-propyl} 4-(2,3-dichlorophenyl)-1,4-dihydro-2,6-dimethylpyridine-3,5-dicarboxylate, 3-methyl 5-{3-[3-(4,4-diphenylpiperid-1-yl)-propoxy]-propyl} 4-(2,1,3-benzoxadiazol-4-yl)-1,4-dihydro-2,6-dimethylpyridine-3,5-dicarboxylate, 3-methyl 5-{3-[3-(4,4-diphenylpiperid-1-yl)-propoxy]-propyl} 4-(3-cyanophenyl)-1,4-dihydro-2,6-dimethyl-pyridine-3,5-dicarboxylate, 3-methyl 5-{3-[3-(4,4-diphenylpiperid-1-yl)-propoxy]-propyl} 1,4-dihydro-2,6-dimethyl-4-(2-methoxyphenyl)-pyridine-3,5-dicarboxylate, 3-methyl 5-{3-[3-(4,4-diphenylpiperid-1-yl)-propoxy]-propyl} 1,4-dihydro-2,6-dimethyl-4-(2-pyridyl)-pyridine-3,5-dicarboxylate and 3-methyl 5-{3-[3-(4,4-diphenylpiperid-1-yl)-propoxy]-propyl} 1,4-dihydro-2,6-dimethyl-4-(5-methyl-2-thienyl)-pyridine-3,5-dicarboxylate, and their salts.

The compounds of the formula I have a chirality center in the 4-position in the 1,4-dihydropyridine. The invention therefore relates both to the enantiomers and the diastereomers, where another chirality center exists, and to their mixtures and racemates. Particularly preferred in this connection are those enantiomers, which have in the 4-position in the dihydropyridine the same configuration as the enantiomers (−)-3-ethyl 5-[3-(4,4-diphenylpiperid-1-yl)-propyl] 2-amino-1,4-dihydro-6-methyl-4-(3-nitrophenyl)-pyridine-3,5-dicarboxylate and (−)-3-methyl 5-{2-[2-(4,4-diphenyl-piperid-1-yl)-ethoxy]-ethyl} 1,4-dihydro-2,6-dimethyl-4-(3-nitrophenyl)-pyridine-3,5-dicarboxylate which rotate linearly polarized light of wavelength 589 nm with $[\alpha]_D^{22} = -0.9°$ and $[\alpha]_D^{22} = -56.1°$ (c=1, methanol), respectively.

The invention also relates to a process for the preparation of the compounds according to the invention and their salts. The process is characterized in that 1. for the preparation of compounds of embodiment a amidines of the formula IIa

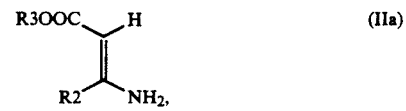

are reacted with benzylidene-carboxylic acid derivatives of the formula (IIIa)

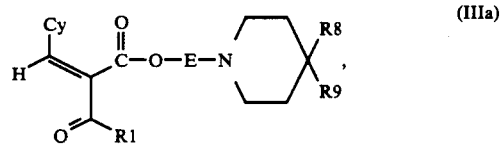

as such or in the form of their salts and, if desired, resulting salts are then converted into the free bases or resulting bases are converted into the salts, Cy, E, R1, R2, R3, R4, R5, R8 and R9 having the meanings mentioned for the embodiment a.

The process is furthermore characterized in that 2. for the preparation of compounds of embodiment b a) cinnamic acid derivatives of the formula IIb

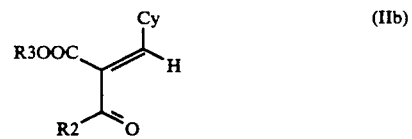

are reacted with enamine derivatives of the formula IIIb

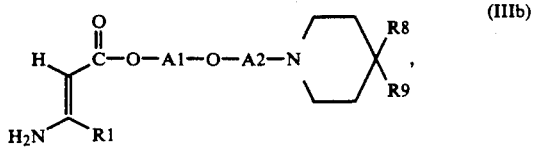

or b) cinnamic acid derivatives of the formula IIb are reacted with ammonia and β-ketocarboxylic acid derivatives of the formula IV

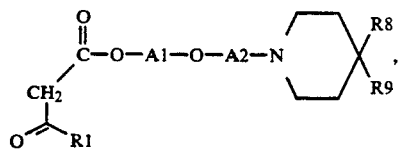

(IV)

or c) enamines of the formula V.

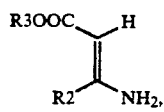

(V)

are reacted with benzylidenecarboxylic acid derivatives of the formula VI

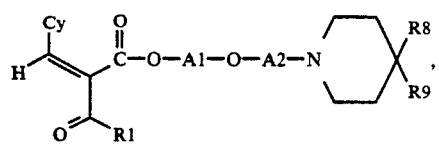

(VI)

or d) keto compounds of the formula VII

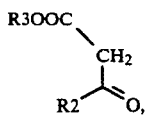

(VII)

are reacted with ammonia and benzylidenecarboxylic acid derivatives of the formula VI, or e) aldehydes of the formula VIII

(VIII)

are reacted with enamines of the formula V and β-ketocarboxylic acid derivatives of the formula IV, or f) aldehydes of the formula VIII are reacted with enamine derivatives of the formula IIIb and keto compounds of the formula VII, or g) 1,4-dihydropyridines of the formula IX

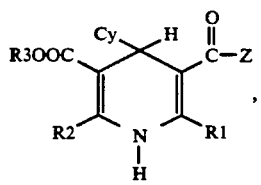

(IX)

are reacted with amine derivatives of the formula X

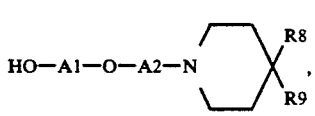

(X)

or h) 1,4-dihydropyridine derivatives of the formula XI

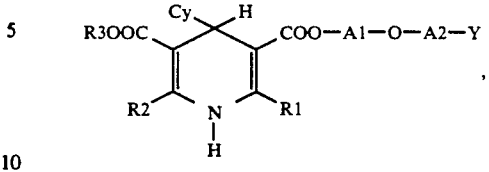

(XI)

are reacted with amines of the formula XII

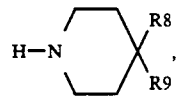

(XII)

as such or in the form of their salts, and, if desired, salts obtained are then converted into the free bases or bases obtained are converted into the salts, wherein Cy, A1, A2, R1, R2, R3, R4, R5, R8 and R9 have the meanings mentioned for the embodiment b, Z, together with the carbonyl group to which it is bonded, represents a carboxyl group or a reactive carboxylic acid derivative of (for example a carboxylic acid halide) and Y represents a leaving group.

Embodiments of the process are those in which the substituents and symbols Cy, E, A1, A2, R1, R2, R3, R4, R5, R8 and R9 in the formulae IIa, IIb, IIIa, IIIb, and IV to XII have the meanings given in the subclaims and independent claims, Z, together with the carbonyl group to which it is bonded, represents a carboxyl group or a reactive carboxylic acid derivative and Y represents a leaving group.

The process according to 1. and 2. is carried out in suitable, preferably inert solvents. Examples which may be mentioned are alcohols, such as ethanol, methanol, isopropanol or, in particular, t-butanol, hydrocarbons, such as toluene or xylene, ethers, such as dioxane, diethyl ether, tetrahydrofuran, glycol monoethyl ether or glycol dimethyl ether, or others, for example polar solvents, such as dimethylformamide, dimethyl sulfoxide, acetonitrile or hexamethylphosphoric acid triamide, or chlorinated hydrocarbons, such as methylene chloride, chloroform or tetrachloroethylene.

The reaction temperatures can be varied within a wide range—depending on the reactivity of the educts. The reaction is in general carried out at temperatures between 20° C. and 150° C., preferably between 20° C. and 100° C. and in particular at the boiling point of the solvent used.

The process according to 1 is carried out in the presence of a basic condensing agent, for example in the presence of an alkali metal alcoholate, such as sodium methylate or sodium ethylate.

The process according to 2 is carried out under normal pressure or under increased pressure, working under normal pressure being the rule, and it being possible to use increased pressure, in particular, in the case of reactions with ammonia.

In carrying out the process according to the invention in accordance with variants a to f, the substance participating in the reaction are as a rule in each case employed in molar amounts, but—depending on the reaction condition —if desired an excess (for example of ammonia in the case of variants b and d) can also be employed.

Similar reaction conditions to those for variants a to f are used in carrying out the process by variant g, but additional measures may be necessary—depending on the nature of the substituent Z. For example, if Z represents a hydroxyl group, the reaction is preferably to be carried out in the presence of a dehydrating or water-blinding condensing agent (such as, for example, dicyclohexylcarbodiimide). If Z represents a halogen atom (for example a chlorine atom), the reaction is to be carried out, if desired, in the presence of a base (for example a tertiary organic amine, such as triethylamine, or an inorganic carbonate, such as sodium carbonate).

Similar reaction conditions to those for variants a to f are used in carrying out the process in accordance with variant h. The reaction is carried out in a manner such as is known for the preparation of secondary and tertiary amines. If desired, the reaction can be carried out in the presence of a base (for example an inorganic carbonate, such as potassium carbonate), or by using an excess of amine XII, depending on the nature of the leaving group Y, which is preferably a halogen atom, in particular a chlorine or bromine atom.

The pure enantiomers of the compounds of formula I and their salts, which are likewise the subject matter of the invention, are obtained for example when the racemates obtained according to 1. or 2. are reacted with a pure enantiomer of an optically active acid, the resulting diastereomeric salts are separated, and the enantiomers are liberated from the desired diastereomeric salt by adding a base, and are, if desired, subsequently converted into their salts.

Examples of optically active acids which may be mentioned are di-0,0'-p-toluoyltartaric acid or, in particular, di-0,0'-benzoyltartaric acid. A suitable separation process is preferably recrystallization.

The diastereomeric salts of uniform configuration which have been separated by means of these methods are converted into the pure enantiomers of the compound according to the invention, preferably by adding inorganic bases, such as, for example, ammonia, or by means of basic ion exchangers.

This process for the preparation of pure enantiomers is preferably used for the preparation of pure enantiomers of compounds of embodiment a.

Alternatively, the pure enantiomers of the compounds according to the invention are obtained by using enantiomer pure starting compounds. In this connection the pure enantiomers of compounds of formula IX have to be singled out, which yield, by reacting them with amine derivatives X according to process variant g, the desired end products. This way is used in particular for preparing the pure enantiomers of the compounds of embodiment b.

The substances obtained according to 1. and 2. are isolated and purified in a manner which is known per se, for example by distilling off the solvent in vacuo and recrystallizing the resulting residue from a suitable solvent, or subjecting it to one of the customary purification methods, such as, for example, column chromatography on a suitable support.

Acid addition salts are obtained by dissolving the free base in a suitable solvent, for example in a chlorinated hydrocarbon, such as methylene chloride or chloroform, or a low molecular weight aliphatic alcohol (ethanol or isopropanol) containing the desired acid or to which the desired acid is subsequently added.

The salts are isolated by filtration, reprecipitation, precipitation with a non-solvent for the addition salt or evaporation of the solvent.

Salts obtained can be converted into the free bases by rendering them alkaline, for example with aqueous ammonia solution, and the bases can in turn be converted into acid-addition salts. Pharmacologically-unacceptable acid-addition salts can in this way be converted into pharmacologically-acceptable acid-addition salts.

The starting compounds are known from the literature or can be prepared by methods which are analogous to those known from the literature. The benzylidenecarboxylic acid derivatives IIIa can be prepared, for example, by a process analogous to that of G. Jones ("The Knoevenagel Condensation" in Org. Reactions, vol. XV, 204f (1967)). The amidines IIa can be prepared in accordance with the method of H. Yamanada et al., Heterocycles 1976, 1854.

The cinnamic acid derivatives IIb and the benzylidenecarboxylic acid derivatives VI can be prepared, for example, by a process analogous to that of G. Jones ["The Knoevenagel Condensation" in Org. Reactions, vol. XV, 204 et seq. (1967)]. The enamine derivatives IIIb and the enamines V are obtainable, for example, by a method analogous to that of A. C. Cope [J. Amer. Chem. Soc. 67, 1017 (1945)]. $\beta$-Ketocarboxylic acid derivatives IV and keto compounds VII can be prepared in accordance with the method of D. Borrmann ["Umsetzung von Diketen mit Alkoholen, Phenolen und Mercaptanen" ("Reaction of Diketene with Alcohols, Phenols and Mercaptans") in Houben-Weyl, Methoden der Organischen Chemie (Methods of Organic Chemistry), vol. VII/4 230 et seq. (1968)] of Y. Oikawa et al. [J. Org. Chem. 43, 2087 (1978)]. The compounds IX are accessible from corresponding starting compounds by methods analogous to process variants a to f. The pure enantiomers of compounds IX which are needed for the preparation of pure enentiomers of the compounds according to the invention are known from Chem. Pharm. Bull. 28, 2809 (1980) or can be obtained analogously.

Compounds X are obtainable by reacting of corresponding piperidines with omega-halogenoalkanols. The dihydropyridine derivatives XI are obtained by reaction of enamines of the formula V with, for example, appropriately substituted omega-halogeno-2-acylacrylic acid esters, which are in turn accessible from aldehydes of the formula VIII and suitable beta-keto-omega-halogeno-carboxylic acid esters.

The above preparation process is given merely for illustration, and the preparation of the compounds of the formula I according to the invention is not limited to this process. Rather, any modification of this process can also be used in the same manner for preparation of the compounds according to the invention.

The following preparation examples are intended to illustrate the invention in more detail without limiting it. M.p. denotes melting point, h represents hours, b.p. represents boiling point and decomp. denotes decomposition.

EXAMPLES

End products

1. 3-Methyl 5-{2-[2-(4,4-diphenylpiperid-1-yl)-ethoxy]-ethyl}1,4-dihydro-2,6-dimethyl-4-(3-nitrophenyl)-pyridine-3,5-dicarboxylate hydrochloride 5.4 g of 2-[2-(4,4-diphenylpiperid-1-yl)-ethoxy]-ethyl 2-acetyl-3-(3-nitrophenyl)-acrylate and 1.2 g of methyl 3-aminocrotonate are heated at the boiling point under reflux in 50 ml of 2-propanol and 0.5 ml of acetic acid for 5 h. The cooled solution is concentrated to dryness, the solid foamed residue is dissolved in a little methylene chloride and the solution is chromatographed over 3×20 cm of silica gel (eluant: methylene chloride/methanol/acetic acid 9+1+1). The product fraction is concentrated, the residue is taken up in methylene chloride and etherial hydrochloric acid is added. After renewed concentration of the product solution, the residue is dissolved in about 10 ml of methylene chloride and the title compound is precipitated as an amorphous solid by slow dropwise addition to 500 ml of a well-stirred mixture of equal parts of diethyl ether and petroleum ether. M.p.: 124°–138° C., yield: 4.9 g.

2. 3-Methyl 5-{2-[2-(4,4-dephenylpiperid-1-yl)-ethoxy]-ethyl}(−)-1,4-dihydro-2,6-dimethyl-4-(3-nitrophenyl)-pyridine-3,5-dicarboxylate hydrochloride 3 ml of oxalyl chloride are added to 997 mg of 3-methyl (−)-1,4-dihydro-2,6-dimethyl-4-(3-nitrophenyl)-pyridine-3,5-dicarboxylate. The mixture is stirred at room temperature until no further evolution of gas can be detected. The batch is concentrated to dryness three times with the addition of 5 ml of absolute toluene each time. The resulting brown solid residue is suspended in 3 ml of absolute methylene chloride and the suspension is added dropwise to a solution, cooled to 0° C., of 1.09 g of N-[ 2-(2-hydroxyethoxy)-ethyl]-4,4-diphenylpiperidine and 0.6 ml of triethylamine, while gassing with $N_2$. After the dropwise addition, the mixture is stirred at room temperature for a further 2 h and then concentrated to dryness. The brownish residue which remains is taken up in 100 ml of methylene chloride and extracted three times with 50 ml of water each time. After the organic phase has been dried over sodium sulfate, the brownish clear solution is substantially concentrated and the oil residue is chromatographed over a 2×30 cm silica gel column with methylene chloride/ethanol (98+2) as the eluting agent. After the chromatographically uniform product fraction has been concentrated, the yellowish residue which remains is taken up in 5 ml of methylene chloride, and ethereal hydrochloric acid is added to the solution. After renewed concentration of the hydrochloride solution to dryness, the residue in the form of a solid foam is dissolved in 3 ml of methylene chloride and the product is precipitated as an amorphous substance by dropwise addition of the solution to 1 l of petroleum ether/diethyl ether (2+1). After the precipitate has been filtered off with suction and dried, the title compound is obtained as a fine gray powder of m.p.: 118°–128° C. (slow deliquescence); $[\alpha]_D^{22} = -0.9°$ (c=1, methanol); yield: 490 mg.

3. 3-Methyl 5-{2-[2-(2-(4,4-diphenylpiperid-1-yl)-ethoxy)-ethoxy]-ethyl}1,4-dihydro-2,6-dimethyl-4-(3-nitrophenyl)-pyridine-3,5-dicarboxylate hydrochloride hydrate From 4,54 g of 2-[2-(2-(4,4-Diphenylpiperid-1-yl)-ethoxy)-ethoxy]-ethyl acetoacetate, 1.41 g of 3-nitrobenzaldehyde and 1.20 g of 3-aminocrotonic acid in 80 ml of 2-propanol and 0.5 ml of glacial acetic acid are obtained after analogous reaction of the starting compounds and working up of the reaction mixture, as described in Example 1, the title compound as an amorphous powder of m.p.: 106°–115° C. (slow deliquescence); yield: 2.5 g.

4. 3-Ethyl 5-[3-(4,4-diphenylpiperid-1-yl)-propyl]2-amino-1,4-dihydro-6-methyl-4-(3-nitrophenyl)-pyridine-3,5-dicarboxylate A sodium ethylate solution prepared from 0.46 g of sodium and 20 ml of ethanol is added dropwise at the boiling point to a solution of 5.49 g of [3-(4,4-diphenylpiperid-1-yl)-propyl] 2-acetyl-3-(3-nitrophenyl)-acrylate hydrochloride and 1.67 g of ethyl amidinoacetate hydrochloride in 15 ml of ethanol in the course of 60 minutes and the mixture is then boiled under reflux for about a further 30 minutes. After the reaction mixture has been concentrated, the resulting residue is partitioned between ethyl acetate, sodium bicarbonate solution and then water. After drying over sodium sulfate, the organic phase is concentrated and the residue is chromatographed over a 3×30 cm silica gel column with methylene chloride/ethanol (95+5) as the eluant. The product fraction is concentrated and the solid foamed residue is taken up in a little methanol. After addition of diethyl ether/petroleum ether (1+1) until slight clouding first persists, the mixture is left to stand in a refrigerator for 24 h. The title compound crystallizes out in the form of fine platelets of m.p. 174°–175° C. Yield: 4.4 g.

5. 3-Ethyl 5-[3-(4,4-diphenylpiperid-1-yl)-propyl](−)-2-amino-1,4-dihydro-6-methyl-4-(3-nitrophenyl)-pyridine-3,5-dicarboxylate 10 g of the racemate from Example 4 and 6.02 g of D-(+)-0,0'-dibenzoyltartaric acid hydrate are dissolved in 300 ml of chloroform at the boiling point. After addition of 50 ml of ethyl acetate, the solution is allowed to cool slowly. A first crystalline product (10 g) is obtained and, after filtration with suction at the boiling point, is recrystallized from a mixture of chloroform/methanol (4+1). The second crystalline product (8.5 g) obtained after cooling is recrystallized again from the above solvent mixture. The 0,0'-dibenzoyltartrate of the titled compound is obtained as coarse yellowish needles of m.p.: 178°–179° C. (decomposition); $[\alpha]_D^{22} = 10.3°$ (c=1, methanol); yield: 4.1 g. The salt is dissolved in 300 ml of methylene chloride and the solution is extracted with 200 ml of concentrated ammonia solution and then three times with 100 ml of water each time. After the organic phase has been dried over sodium sulfate, it is concentrated. The solid residue which remains is dissolved in 5 ml of methylene chloride and the product is precipitated as an amorphous substance by dropwise addition of the solution to 1 l of petroleum ether. Filtration with suction gives the title compounds as a yellowish fine powder of m.p.: 96°–104° C. (slow deliquescence); $[\alpha]_D^{22} = 56.1°$ (c=1, methanol); yield: 2.31 g.

6. 3-Ethyl 5[5-(4,4-diphenylpiperid-1-yl)-pentyl 2-amino-1,4-dihydro-6-methyl-4-(3-nitrophenyl)-pyridine-3,5-dicarboxylate The title compound is obtained analogously to Example 4 from 3.60 g of 5-(4,4-diphenylpiperid-1-yl)-pentyl acetyl-3-(3-nitrophenyl)-acrylate, 1.11 g of ethyl amidinoacetate hydrochloride and 0.153 g of sodium in 17 ml of absolute ethanol, after a reaction time of 2 h, as a gray powder of m.p.: 98°–120° C. (slow deliquescence; precipitated as an amorphous substance from petroleum ether); yield: 1.97 g.

7. 3-Ethyl 5-[3-(4,4-diphenylpiperid-1-yl)-propyl]2-amino-4-(2,3-dichlorophenyl)-1,4-dihydro-6-methylpyridine-3,5-dicarboxylate semifumarate The title compound is obtained analogously to Example 4 from 5.00 g of 3-(4,4-diphenylpiperid-1-yl)-propyl 2-acetyl-3-(2,3-dichlorophenyl)-acrylate, 1.55 g of ethyl amidinoacetate hydrochloride and 210 mg of sodium in 25 ml of absolute ethanol, after conversion into the semifumarate, as hard cubic crystals of m.p.: 191°–93° C. (from methanol/diethyl ether); yield: 5.05 g.

8. 3-Ethyl 5-[3-(4,4-diphenylpiperid-1-yl)-propyl] 2-amino-4-(4-benzo[c][1.2.5]oxadiazolyl)-1,4-dihydro-6-methyl-pyridine-3,5-dicarboxylate The title compound is obtained analogously to Example 4 from 6.11 g of 3-(4,4-diphenylpiperid-1-yl)-propyl 2-acetyl-3-(4-benzo[c][1.2.5]oxadiazolyl)-acrylate, 2.01 g of ethyl amidinoacetate hydrochloride and 276 mg of sodium in 35 ml of absolute ethanol, as fine yellowish crystal platelets of m.p.: 127°–131° C. [slow deliquescence, from methanol/diethyl ether); yield: 2.7 g.

9. 3-Ethyl-5-[3-(4,4-diphenylpiperid-1-yl)-propyl 2-amino-4-(2-chlorophenyl)-1,4-dihydro-6-methyl-pyridine-3,5-dicarboxylate The title compound is obtained analogously to Example 4 from 4.02 g of 3-(4,4-diphenylpiperid-1-yl)-propyl 2-acetyl-3-(2-chlorophenyl)-acrylate, 1.33 g of ethyl amidinoacetate hydrochloride and 184 mg of sodium in 50 ml of absolute ethanol, as fine yellowish crystal platelets of m.p.: 125°–128° C. (from methanol/diethyl ether); yield: 2.71 g.

10. 3-Ethyl 5-[3-(4,4-diphenylpiperid-1-yl)-propyl]2-amino-1,4-dihydro-6-methyl-4-(2-trifluoromethylphenyl)-pyridine-3,5-dicarboxylate The title compound is obtained analogously to Example 4 from 4.28 g of 3-(4,4-diphenylpiperid-1-yl)-propyl 2-acetyl-3-(2-trifluoromethylphenyl)-acrylate, 1.33 g of ethyl amidinoacetate hydrochloride and 184 g of sodium in 40 ml of absolute ethanol, as fine yellowish crystal platelets of m.p.: 115°–117° C. (from methanol/diethyl ether), yield: 3.32 g.

11. 3-Methyl 5-[2-(4,4-diphenylpiperid-1-yl)-ethyl] 2-amino-1,4-dihydro-6-methyl-4-(3-nitrophenyl)-pyridine-3,5-dicarboxylate The title compound is obtained analogously to Example 4 from 4.98 g of 2-(4,4-diphenylpiperid-1-yl)-ethyl 2-acetyl-3-(3-nitrophenyl)-acrylate, 1.52 g of methyl amidinoacetate hydrochloride and 230 mg of sodium in 40 ml of absolute methanol, as a fine yellowish powder of m.p.: 110°–116° C., slow deliquescence, (precipitated from petroleum ether/diethyl ether (2+1); yield: 3.12 g.

Starting compounds

A. 2-[2-(4,4-diphenylpiperid-1-yl)-ethoxy]-ethyl 2-acetyl-3-(3-nitrophenyl)-acrylate 4.1 g of 2-[2-(4,4-diphenylpiperid-1-yl)-ethoxy]-ethyl acetoacetate, 15 g of 3-nitrobenzaldehyde, 8 ml of acetic acid and 0.5 ml of piperidine are heated at the boiling point in 300 ml of toluene using a water separator. After 1.9 ml of water have been separated off, the cooled solution is washed with saturated sodium bicarbonate solution and then with water. After the organic phase has been dried with sodium sulfate, the clear reddish-brown solution is concentrated under a high vacuum. The resulting viscous residue is used for the condensation reaction, without further purification. Yield: 53 g of crude product as a cis/trans-isomer mixture. Other entraining agents which are suitable are: benzene and chlorinated hydrocarbons. The yield of crude product is 95–100% of theory.

B. 2-[2-(4,4-Diphenylpiperid-1-yl)-ethoxy]-ethyl acetoacetate 20 ml of a 50% strength solution of diketene in acetone are added dropwise to 32.5 g of N-[2-(2-hydroxyethoxy)-ethyl]-4,4-diphenylpiperidine and about 0.1 g of N,N-dimethylaminopyridine in 200 ml of methylene chloride at the boiling point, with vigorous stirring. After boiling under reflux for 1 h, the solution is allowed to cool and is concentrated to constant weight under a high vacuum. The pale yellow viscous coil which remains is used for the next stage without further purification.

2-{2-[2-(4,4-Diphenylpiperid-1-yl)-ethoxy]-ethoxy}-ethyl acetoacetate is obtained analogously, starting from triethylene glycol monochlorohydrine and with the preceding reaction as described under C.

C. N-[2-(2-Hydroxyethoxy)-ethyl]-4,4-diphenylpiperidine 82 g of 4,4-diphenylpiperidine, 50 g of diethylene glycol monochlorohydrin, 250 g of finely powdered potassium carbonate and 1 g of potassium iodide are heated at the boiling point under reflux, with vigorous stirring, in 1.2 l of a 1:1 mixture of dioxane and 1-butanol for 50 h. After cooling, the mixture is filtered and the filtrate is concentrated. The oily residue is taken up in ethyl acetate and the solution is filtered again. After the filtrate has been concentrated to constant weight (high vacuum), the title compound is obtained as a waxy viscous residue. Yield: 106 g. The hydrochloride is obtained with ethereal hydrochloric acid and is recrystallized from 2-propanol. M.p.: 120°–121° C.

The preparation of further starting compounds is described e.g. in European patent application 176 956.

Commercial usefulness

The compounds of the formula I according to the invention and their salts have useful properties which render them commercially useful. In particular, they are active vasodilators with coronary therapeutic properties. The pharmacological activity of the compounds according to the invention manifests itself in particular in a marked reduction in blood pressure which starts slowly and which has an optimum duration. The compounds according to the invention moreover have an inhibiting action on the flow of calcium into and a promoting action on the flow of potassium out of cells, relaxing properties on smooth muscle and dilating properties on peripheral, coronary, cerebral and renal vessels, as well as salidiuretic, antithrombotic, antiarteriosclerotic and favorable hemorheological properties.

The compounds according to the invention differ surprisingly and advantageously from the compounds of the prior art in their excellent activity, coupled with a low toxicity and a lack of substantial side effects.

Examples which may be mentioned of advantageous properties of the compounds I are: the degree of reduction in blood pressure, the easy controllability of the reduction in blood pressure, the surprisingly low increase in heart rate—in particular for the compounds of embodiment a—in comparison with the compounds of the prior art, the excellent bioavailability, the wide therapeutic range, the lack of central side effects, the lack of kinetic interactions with other substances, the absence of tolerance development, the balanced physical properties and the high stability.

The excellent activity of the compounds of formula I according to the invention and their salts enables them to be used in human medicine, suitable indications being, in particular, primary (essential) and secondary, arterial and pulmonary hypertension of all degrees of severity, coronary heart diseases (coronary insufficiency, angina pectoris, myocardial infarction etc.), disturbances in peripheral and cerebral circulation (strokes, temporary cerebral circulatory disturbances, migraine, dizziness, narrowing of the renal arteries and the like), hypertrophic cardiomyopathy, cardiac insufficiency, diseases based on an increased retention of water and sodium and diseases based on an increased inflow of calcium, such as, for example, spasms of smooth muscle organs (respiratory tract, gastrointestinal tract, urogenital tract and the like), as well as arrhythmia and arteriosclerosis.

The invention thus also relates to a process for the treatment of mammals, in particular humans, suffering from one of the abovementioned diseases. The process is characterized in that a therapeutically-effective and pharmacologically-acceptable amount of one or more compounds of the formula I is administered to the sick individual.

The invention also relates to the compounds of the formula I for use in the treatment of the diseases mentioned.

The invention likewise relates to the use of compounds of the formula I in the preparation of medicaments used for combating the diseases mentioned.

The invention also relates to medicaments containing one or more compounds of the general formula I.

The medicaments are prepared by processes which are known per se and with which the expert is familiar. As medicaments, the pharmacologically-active compounds (=active substances) according to the invention are used either as such or, preferably, in combination with suitable pharmaceutical auxiliaries, in the form of tablets, coated tablets, capsules, suppositories, plasters (for example as transdermal therapeutic systems), emulsions, suspensions, aerosols, sprays, ointments, creams, gels or solutions, the content of active substance advantageously being between 0.1 and 95%.

The expert is familiar with what auxiliaries are suitable for the desired medicament formulations on the basis of his expert knowledge. As well as solvents, gel-forming agents, suppository bases, tablets, auxiliaries and other active substance carriers, it is possible to use, for example, antioxidants, dispersing agents, emulsifiers, foam suppressants, flavor correctants, preservatives, solubilizing agents, dyestuffs or, in particular, permeation promoters and complexing agents (for example cyclodextrins).

The active substances can be administered orally, rectally, by inhalation or parenterally (in particular perlingually, intravenously or percutaneously).

In general, it has proven advantageous in human medicine, in the case of oral administration, to administer the active substance or substances in a daily dose of about 0.01 to about 10, preferably 0.05 to 5 mg/kg of body weight, if desired in the form of several, preferably 1 to 4, individual doses, to achieve the desired result. In the case of parenteral treatment, similar or (in particular in the case of intravenous administration of the active substances) as a rule lower dosages can be used. If the dosage is increased gradually, a lower dose is administered at the start of treatment and is then slowly changed to a higher dose. When the desired therapeutic result has been achieved, the dose is reduced again.

The particular optimum dosage required and the mode of administration of the active substances can easily be determined by any expert on the basis of his expert knowledge.

If the compounds according to the invention and/or their salts are to be used for the treatment of the diseases mentioned, the pharmaceutical formulations can also contain one or more other pharmacologically-active constituents from other groups of medicaments, such as other vasodilators, antihypertensives, alpha-1-receptor blockers, alpha-2-receptor stimulators, beta-1-receptor blockers, beta-2-receptor stimulators, ACE inhibitors, nitro compounds, cardiotonics, diuretics, saluretics, alkaloids, analgesics, lipid-lowering agents, anticoagulants, anticholinergics, methylxanthines, antiarrhythmics, antihistamines, dopamine stimulators, serotonin receptor blockers and the like, such as nifedipine, dihydralazine, prazosin, clonidine, atenolol, labetalol, fenoterol, captopril, isosorbide dinitrate, digoxin, milrinon, mefruside, clopamide, spironolactone, chlorthalidone, furosemide, polythiazide, hydrochlorothiazide, reserpine, dihydroergocristine, rescinnamine, Rauwolfia total alkaloids, acetylsalicylic acid, bezafibrate, warfarin, atropine, theophylline, lidocaine, astemizole, bromocryptine, ketanserin and the like.

Pharmacology

The antihypertensive activity of the compounds according to the invention can be demonstrated by the model of the spontaneously hypertensive rat.

To determine the antihypertensive action, the compounds shown below are administered once daily by means of a stomach tube in the stated doses on four successive days to in each case 6 male rats (strain SHR/N/Ibm/Bm 250-350 g) with hypertension (systolic blood pressure > 180 mmHg) of genetic origin. The blood pressure is in each case measured 6 and, if appropriate, 2 or 24 hours after administration of the substance.

The blood pressure measurement is carried out in a warming chamber at 36° C. in order to achieve better circulation of the tail artery. For this, the animals are placed in perforated metal cages and measured 20-40 minutes after the start of warming. To measure the systolic arterial pressure, an annular cuff with an inflatable rubber membrane to suppress the circulation and an annular piezocrystal transducer to record the pulse waves are pushed onto the tail. When the blood stream has been suppressed in the tail artery, the cuff pressure is reduced continuously. The return of the pulse waves as the pressure decreases is detected and printed out automatically as the systolic blood pressure (Bühler, R. et al.: Microprocessor-based automation of blood pressure measurement in the conscious rat. Proceedings of the 4th international symposium on rats with spontaneous hypertension and related studies, Rascher, R. et al. (Eds.), Schattauer Verlag, Stuttgart, New York, 1982, pages 410–413). The pulse signals and pressure curve are recorded graphically for evaluation.

For acclimatization to the measurement operation, the animals are trained for 14 days before the substance trial. Blood pressure prevalues are recorded in the second week of training. Animal groups receiving the substance are tested against a control group.

The compounds investigated are identified by serial numbers in the subsequent table which correspond to the numbers in the Examples.

Table I shows the percentage reduction in blood pressure (BP) for representatives of the compounds according to the invention following oral administration to rats.

TABLE I

| % changes (BP) on genetically hypertensive rats following a single daily peroral ← administration on four successive days (N = 6/dose). | | | |
|---|---|---|---|
| | | BP (% change versus control) mean value for measurement times: hours after administration (days) | |
| Serial No. | Dose µmol/kg | 2 h (1st + 4th day) | 6 h (1st 4th day) | 24 h (1st + 3rd day) |
| 1 | 25 | −49.0 | −30.0 | −4.0 |
| 2 | 25 | −45.5 | −34.0 | −5.0 |
| 4 | 25 | −53.5 | −49.0 | −33.5 |
| 6 | 25 | −20.0 | −30.3 | −4.5 |
| 7 | 25 | −10.0 | −29.5 | −3.5 |

I claim:
1. A compound of formula I

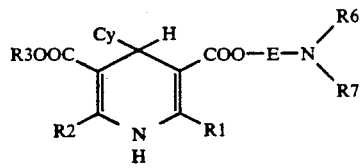

wherein Cy represents a cyclic radical of the formula

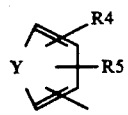

in which Y denotes vinylene (—CH═CH—), azomethine (—CH═N—), or

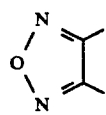

R1 denotes hydrogen, 1–6C-alkyl or 3–7C-alkoxyalkyl,

R4 and R5 are identical or different and denote hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, R6 and R7, together and including the nitrogen atom to which the two are bonded, represent a radical of the formula

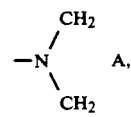

wherein
A denotes —CH₂—C(R8)R9—CH₂—,
R8 denotes aryl and
R9 denotes aryl,
aryl representing a ring of the formula

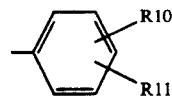

wherein R10 and R11 are identical or different and denote hydrogen (H), 1–4C-alkyl, 1–4C-alkoxy, halogen, hydroxyl or trifluoromethyl, and wherein either E denotes 2–5C-alkylene,
R2 denotes amino (NH₂) and
R3 denotes 1–6C-alkyl or 3–7C-alkoxyalkyl,
or
E denotes A1-O-A2,
R2 denotes hydrogen, 1–6C-alkyl or 3–7C-alkoxyalkyl and
R3 denotes hydrogen, 1–6C-alkyl or 3–7C-alkoxyalkyl and
in which
A1 denotes 2–4C-alkylene and
A2 denotes 2–4C-alkylene or 2C-alkyleneoxy-2C-alkylene,
or a pharmacologically-acceptable salt thereof.

2. A compound of claim 1 formula Ia

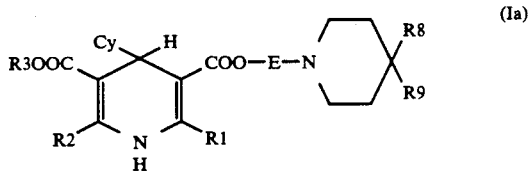

wherein Cy represents a cyclic radical of the formula

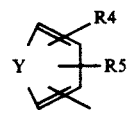

in which Y denotes vinylene (—CH═CH—), azomethine (—CH═N—) or a group of the formula

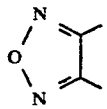

E denotes 2–5C-alkylene,

R1 denotes hydrogen, 1–6C-alkyl or 3–7C-alkoxyalkyl,

R2 denotes amino (NH₂),

R3 denotes 1–6C-alkyl or 3–7C-alkoxyalkyl,

R4 and R5 are identical or different and denote hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, R8 denotes aryl and R9 denotes aryl, aryl representing a ring of the formula

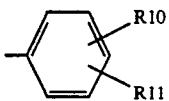

wherein R10 and R11 are identical or different and denote hydrogen (H), 1–4C-alkyl, 1–4C-alkoxy, halogen, hydroxyl or trifluoromethyl, or a pharmacologically-acceptable salt thereof.

3. A compound of formula Ia according to claim 2, wherein

Cy denotes 3-nitrophenyl, 2-chlorophenyl, 2,3-dichlorophenyl, 2-trifluoromethylphenyl or benzoxadiazolyl, E denotes ethylene (—CH₂—CH₂—), trimethylene (—CH₂—CH₂—CH₂—) or pentamethylene (—CH₂—CH₂—CH₂—CH₂—CH₂—), R1 denotes methyl, R2 denotes amino (NH₂), R3 denotes methyl or ethyl, R8 denoted phenyl; and R9 denotes phenyl or a pharmacologically-acceptable salt thereof.

4. A compound of claim 1 formula Ib

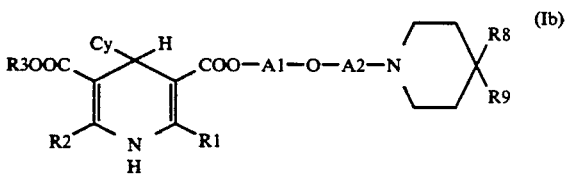

wherein Cy represents a cyclic radical of the formula

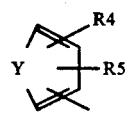

in which Y denotes vinylene (—CH=CH—), azomethine (—CH=N—) or a group of the formula

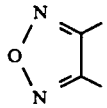

A1 denotes 2–4C-alkylene,

A2 denotes 2–4C-alkylene or 2C-alkyleneoxy-2C-alkylene,

R1 and R2 are identical or different and denote hydrogen, 1–6C-alkyl or 3–7C-alkoxyalkyl, R3 denotes hydrogen, 1–6C-alkyl or 3–7C-alkoxyalkyl, R4 and R5 are identical or different and denote hydrogen, hydroxyl, halogen, nitro, cyano, trifluoromethyl, 1–4C-alkyl, 1–4C-alkoxy, 1–4C-alkoxy which is completely or partly substituted by fluorine, 1–4C-alkoxycarbonyl, 2–5C-acyl, amino or mono- or di-1–4C-alkylamino, R8 denotes aryl and R9 denotes aryl, wherein aryl represents a ring of the formula

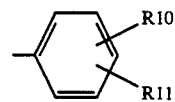

wherein R10 and R11 are identical or different and denote hydrogen (H), 1–4C-alkyl, 1–4C-alkoxy, halogen, hydroxyl or trifluoromethyl, or a pharmacologically-acceptable salt thereof.

5. A compound of formula Ib according to claim 4, wherein

Cy denotes 3-nitrophenyl, 2-chlorophenyl, 2,3-dichlorophenyl, 2-trifluoromethylphenyl or benzoxadiazolyl, A1 denotes ethylene (—CH₂—CH₂—), A2 denotes ethylene (—CH₂—CH₂—) or ethyleneoxyethylene (—CH₂—CH₂—O—CH₂—CH₂—), R1 denotes methyl, R2 denotes methyl, R3 denotes methyl or ethyl, R8 denotes phenyl and R9 denotes phenyl and or a pharmacologically-acceptable salt thereof.

6. A compound of claim 1 selected from the group consisting of

3-Methyl 5-{2-[2-(4,4-diphenylpiperid-1-yl)-ethoxy]-ethyl} 1,4-dihydro-2,6-dimethyl-4-(3-nitrophenyl)-pyridine-3,5-dicarboxylate, 3-Methyl 5-{2-[2-(4,4-diphenylpiperid-1-yl)-ethoxy]-ethyl} (—)-1,4-dihydro-2,6-dimethyl-4-(3-nitrophenyl)-pyridine-3,5-dicarboxylate, 3-Methyl 5-{2-[2-(2-(4,4-diphenylpiperid-1-yl)-ethoxy)-ethoxy]-ethyl} 1,4-di-hydro-2,6-dimethyl-4-(3-nitrophenyl)-pyridine-3,5-dicarboxylate, 3-Ethyl 5-[3-(4,4-diphenylpiperid-1-yl)-propyl] 2-amino-1,4-dihydro-6-methyl-4-(3-nitrophenyl)-pyridine-3,5-dicarboxylate, 3-Ethyl 5-[3-(4,4-diphenylpiperid-1-yl)-propyl] (—)-2-amino-1,4-dihydro-6-methyl-4-(3-nitrophenyl)-pyridine-3,5-dicarboxylate, 3-Ethyl 5-[5-(4,4-diphenylpiperid-1-yl)-pentyl] 2-amino-1,4-dihydro-6-methyl-4-(3-nitrophenyl)-pyridine-3,5-dicarboxylate, 3-Ethyl 5-[3-(4,4-diphenylpiperid-1-yl)-propyl] 2-amino-4-(2,3-dichlophenyl)-1,4-dihydro-6-methyl-pyridine-3,5-dicarboxylate, 3-Ethyl 5-[3-(4,4-diphenylpiperid-1-yl)-propyl] 2-amino-4-(4-benzo[c][1.2.5]-oxadiazolyl-1,4-dihydro-6-methyl-pyridine-3,5-dicarboxylate 3-Ethyl 5-[3-(4,4-diphenylpiperid-1-yl)-propyl] 2-amino-4-(2-chlorophenyl)-1,4-dihydro-6-methyl-pyridine-3,5-dicarboxylate, 3-Ethyl 5-[3-(4,4-diphenylpiperid-1-yl)-propyl] 2-amino-1,4-dihydro-6-methyl-4-(2-trifluoromethyl-phenyl)-pyridine-3,5-dicarboxylate 3-Methyl 5-[2-(4,4-diphenylpiperid-1-yl)-ethyl] 2-amino-1,4-dihydro-6-methyl-4-(3-nitrophenyl)-pyridine-3,5-dicarboxylate;

or a pharmacologically-acceptable salt thereof.

7. A medicament containing a suitable pharmaceutical auxiliary and one or more compounds according to claim 1 and/or a pharmacologically-tolerated salt thereof.

8. A compound according to claim 1 wherein Cy is optionally-substituted phenyl, or a pharmacologically-acceptable salt thereof.

9. A compound according to claim 1 wherein Cy is optionally-substituted pyridyl, or a pharmacologically-acceptable salt thereof.

10. A compound according to claim 1 wherein Cy is optionally-substituted benzoxadiazole, or a pharmacologically-acceptable salt thereof.

11. A method for treatment and/or prophylaxis of hypertension, coronary heart disease, disturbance in peripheral and cerebral circulation and/or disease based on an increased retention of water or sodium which comprises administering an effective amount of a compound according to claim 1 or of a pharmacologically-acceptable salt thereof to a mammal subject to or afflicted with one of the previously-noted conditions.

12. A compound of claim 1 wherein E denotes 2-50-alkylene, or a pharmaceutically-acceptable salt thereof.

UNITED STATES PATENT AND TRADEMARK OFFICE
CERTIFICATE OF CORRECTION

PATENT NO. : 5,064,839
DATED : November 12, 1991
INVENTOR(S) : FLOCKERZI

It is certified that error appears in the above-identified patent and that said Letters Patent is hereby corrected as shown below:

Column 1, line 51, "hydrogen" should read —hydrogen,—; line 65,

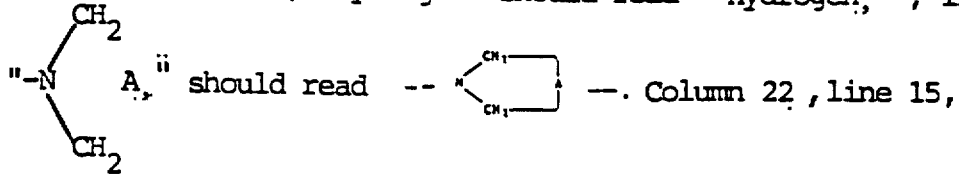. Column 22, line 15,

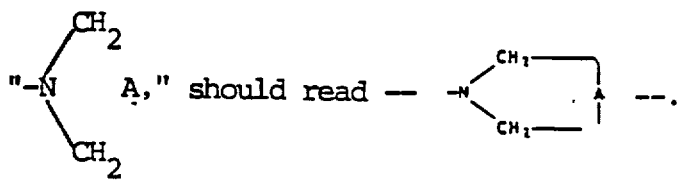

Signed and Sealed this

Second Day of March, 1993

Attest:

STEPHEN G. KUNIN

Attesting Officer    Acting Commissioner of Patents and Trademarks